United States Patent [19]

Quinn et al.

[11] Patent Number: 4,834,712
[45] Date of Patent: May 30, 1989

[54] TUBE FIXATION DEVICE

[75] Inventors: David G. Quinn, Grayslake; Robert B. Edwards, II, Libertyville; Erik Andersen, Vernon Hills; Michael Q. Thompson, Waukegan, all of Ill.

[73] Assignee: Corpak, Inc., Wheeling, Ill.

[21] Appl. No.: 144,470

[22] Filed: Jan. 15, 1988

[51] Int. Cl.[4] ............................................. A61M 5/00
[52] U.S. Cl. .................................. 604/175; 604/174; 128/DIG. 26
[58] Field of Search ................ 604/174, 175, 177–180, 604/29, 905; 128/DIG. 26

[56] References Cited

U.S. PATENT DOCUMENTS

| | | | |
|---|---|---|---|
| 1,696,763 | 12/1928 | Hare | 604/179 |
| 3,241,554 | 3/1966 | Coanda | 128/DIG. 26 |
| 3,253,594 | 5/1966 | Matthews et al. | 128/DIG. 26 |
| 3,568,679 | 3/1971 | Reif | 128/DIG. 26 |
| 3,683,911 | 8/1972 | McCormick | 128/214 |
| 3,856,020 | 12/1974 | Kovac | 128/DIG. 26 |
| 4,261,363 | 4/1981 | Russo | 128/DIG. 26 |
| 4,392,853 | 7/1983 | Muto | 604/180 |
| 4,392,857 | 7/1983 | Beran | 604/179 |
| 4,419,094 | 12/1983 | Patel | 604/180 |
| 4,435,174 | 3/1984 | Redmond et al. | 604/174 |
| 4,449,974 | 5/1984 | Messingschlager | 604/175 |
| 4,516,968 | 5/1985 | Marshall et al. | 604/174 |
| 4,569,675 | 2/1986 | Prosl et al. | 604/175 |
| 4,645,492 | 2/1987 | Weeks | 604/180 |
| 4,668,222 | 5/1987 | Poirier | 604/175 |
| 4,676,782 | 6/1987 | Yamamoto et al. | 604/175 |
| 4,687,470 | 8/1987 | Okada | 604/171 |
| 4,687,471 | 8/1987 | Twardowski et al. | 604/175 |
| 4,701,163 | 10/1987 | Parks | 604/178 |
| 4,717,385 | 1/1988 | Cameron | 604/DIG. 26 |
| 4,743,231 | 5/1988 | Kay et al. | 604/180 |

Primary Examiner—Stephen C. Pellegrino
Assistant Examiner—Ralph Lewis
Attorney, Agent, or Firm—Wallenstein, Wagner & Hattis, Ltd.

[57] ABSTRACT

The invention is a device for angular fixation of a delivery or drainage tube at, for example, the point where that tube exits through the skin from a body cavity. The tube may be used for delivery, extraction, or evacuation of fluids or gases through a surgically formed stoma in a patient. In the enteral feeding, or delivery, embodiment, an enteral feeding tube extends outwardly from the patient to support the components of the device. The components include a sleeve disposed along and movable along the feeding tube and a base elbow unit through which the feeding tube passes. The base elbow unit includes a subdermal portion, a sleeve engaging portion, and a generally cylindrical tube-engaging portion. The feeding tube is movable from a first, substantially straight position to a second, acutely angled position. In this second, acutely angled position, the tube is immobilized by locking engagement to the tube engaging portion. The device includes an interlocking tab at one end of the sleeve, which tab enables locking engagement of the sleeve engaging portion of the base elbow unit when the tube is in its second, acutely angled position.

4 Claims, 1 Drawing Sheet

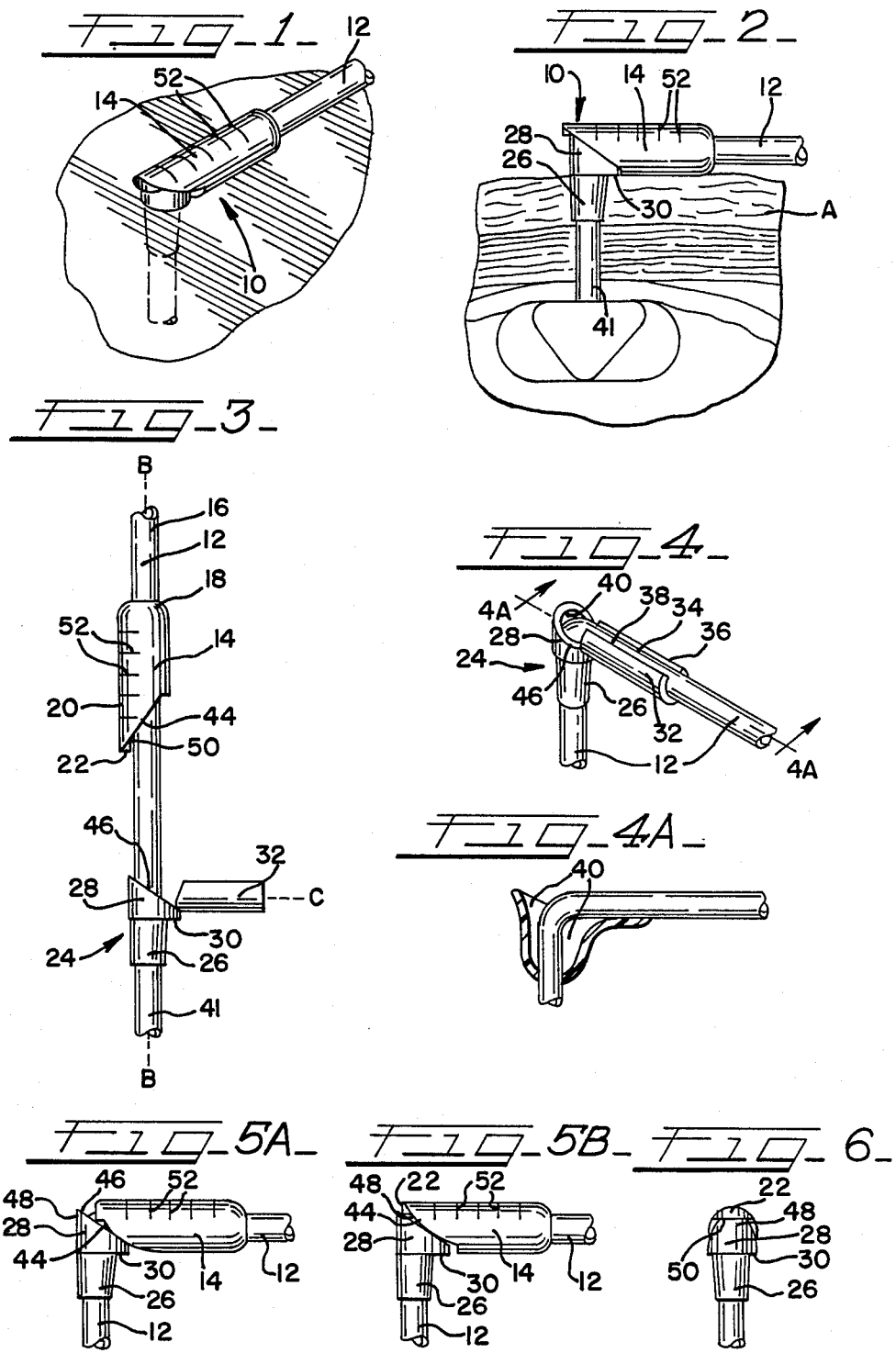

TUBE FIXATION DEVICE

DESCRIPTION

1. Technical Field of the Invention

The present invention generally relates to appliances and devices used in connection with the fixation of a delivery or drainage tube at the point where that tube exits through the skin from a body cavity, such as the peritoneal cavity.

Examples include a gastrostomy tube used for enteral feeding into the stomach; a suprapubic cystostomy tube for draining the bladder; or a continuous peritoneal dialysis catheter used for both instilling and withdrawing fluid from the peritoneal cavity.

2. Background of the Invention

Use of a surgically formed feeding stoma, such as a gastrostomy, is finding increasing acceptance as an alternative procedure in patients requiring long term nutritional support. Gastrostomy enteral feeding is often considered in patients requiring custodial care, such as the elderly, in whom intubation of a nasoesophageal feeding tube is undesirable or impractical.

The problems associated with fixation of a tube on the skin at the point where the tube exits the body through the skin are similar for all of the applications. The use of the tube for a gastrostomy is selected as a typical example to describe the function of the present device.

It is important that the enteral feeding tube, upon intubation through the stoma, be maintained in a relatively stationary and concentric position during enteral feeding.

Hence, prior to the development of the present invention, a need existed for a gastrostomy appliance for supporting a small diameter enteral feeding tube within the stoma of a feeding gastrostomy. A further need existed for an appliance which would maintain the perpendicular position of the enteral feeding tube within the stoma relative to the patient's skin. A need also existed for an enteral feeding tube support appliance which can be easily removed and replaced aobut an external proximal portion of the feeding tube protruding from the gastrostomy.

SUMMARY OF THE INVENTION

The invention is a device for angular fixation of a delivery or drainage tube at, for example, the point where that tube exits through the skin from a body cavity. In the gastrostomy example, the present invention is preferably used to secure a generally circular, deformable, elongated enteral feeding tube. Typically, such a tube includes a feeding inlet end through which the enteral fluid is supplied and an outlet end for discharging that fluid into the patient. The feeding tube extends outwardly from the patient.

One of two components of the preferred embodiment of the present invention is a sleeve which is both disposed and movable along the feeding tube. Initially, it is generally proximate the feeding inlet end of the tube. One end of the sleeve is sized sufficiently small to frictionally engage the tube, but sufficiently large to permit the sleeve to move freely along that tube. The opposite end of the sleeve is known as the interlocking end, for the reason that it interlockingly engages a second component of the present device in a manner to be described later.

The second component of the preferred embodiment of the present invention is a base elbow unit through which the feeding tube passes, and which is disposed along that tube proximate the outlet end. The base elbow unit preferably is molded in one piece, and comprises three main parts. The first part is a subdermal portion, which in normal use by the patient is placed below the skin level. Coaxial with the subdermal portion along a first axis is the second part of the base elbow unit, a sleeve engaging portion for cooperative engagement with the sleeve when the present device is in its fully assembled, operating configuration. The third part of the base elbow unit is a generally cylindrical tube-engaging portion, which is preferably oriented along a second axis perpendicular relative to the first axis. However, it should be understood to those skilled in the art that this second axis and the tube-engaging portion can be at an acute angle, i.e., less than perpendicular or 90 degrees, to the first axis. To ensure a secure, gripping engagement of the deformable feeding tube by the tube-engaging portion, the inner diameter of the tube-engaging portion is slightly smaller than the outer diameter of the feeding tube.

When the feeding tube is in its first, substantially straight position, the feeding tube passes through the subdermal and sleeve engaging portions of the base elbow unit. The feeding tube may be bent into a second, acutely angled position in which the tube also passes through the tube engaging portion of the base elbow unit. In this second, acutely angled position, the feeding tube is immobilized by locking engagement to the tube engaging portion.

The sleeve includes an interlocking tab adjacent its interlocking end. The sleeve and its interlocking tab are movable along the feeding tube and away from the feeding inlet end to a position where the tab may lockingly engage the sleeve engaging portion of the base elbow unit when the tube is in its second, acutely angled position.

To aid the user in securely gripping the sleeve, the sleeve may optionally be provided with one or more circumferential ribs along its outer surface.

BRIEF DESCRIPTION OF DRAWINGS

FIG. 1 is a perspective view of the preferred tube fixation device of the present invention shown secured to the patient's skin;

FIG. 2 is a side view, partially in section, of the preferred tube fixation device of FIG. 1 and a patient's abdominal wall and anterior stomach wall illustrating use and placement of the present invention;

FIG. 3 is a side view of a preferred embodiment of the present invention, including the circular, deformable, elongated enteral feeding tube in its first, substantially straight position, the sleeve with its interlocking tab, and the base elbow unit;

FIG. 4 is perspective view of the base elbow unit and of the feeding tube in its second, acutely angled position;

FIG. 4A is a side view, partially in section and taken along line 4A—4A of FIG. 4, of the base elbow unit and the feeding tube of FIG. 4, and showing the "necked-down" common interior of the sleeve engaging and subdermal portions of the base elbow unit;

FIGS. 5A and 5B are side views of the base elbow unit of FIG. 4, and of the sleeve of the present invention moving progressively towards a position where its interlocking tab may engage the sleeve engaging portion of the base elbow unit; and FIG. 6 is a frontal view of the base elbow unit and sleeve of the present invention, showing the locking engagement of the sleeve's interlocking tab on the sleeve engaging portion of the base elbow unit.

DETAILED DESCRIPTION

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. For example, other embodiments could include wings or flaps used to tape or suture down the device.

Referring now to the drawings, FIGS. 1 and 2 disclose a preferred embodiment of the tube fixation device of the present invention, generally referenced by numeral 10, in its fully assembled configuration. Tube fixation device 10 is generally adhered to the patient's abdominal wall A or other body surface through the use of an adhesive lined bandage (not shown).

Because tube fixation device 10 may have other uses, it should be understood that the device is intended for insertion into any surgically-formed ostomy. For example, device 10 may be used for peritoneal dialysis, suprapubic cystostomy, and gastrostomy.

FIG. 3 discloses the preferred tube fixation device in a disassembled state and carried on a segment of an elongated, generally circular, deformable enteral feeding tube 12. The tube, typically of a diameter between 12 and 22 French, is preferably made of a soft plastic material. "Deformable" in the context of the present invention is intended to mean (1) the ability of the tube to bend along its length, and then return to a straight shape without kinking; and (2) the ability of the tube to compress from its unstressed, normal diameter to a narrower, stressed diameter, and to then return to that normal diameter after the source of stress is removed. This deformable characteristic will be important for reasons which will later become apparent.

One component is a sleeve 14 which is shown proximate the feeding inlet end 16 of the enteral feeding tube 12. The sleeve itself includes two ends, namely a feeding tube-engaging end and a interlocking end. The feeding tube-engaging end 18 is disposed nearest the feeding inlet end 16 of the tube 12. It is sized of a sufficiently small diameter such that it frictionally engages the feeding tube 12. It is also of a sufficiently small diameter such that the sleeve 14 may move readily along the length of the enteral feeding tube 12 when that tube is in the normal, straight position shown in FIG. 3.

The opposite end of the sleeve 14 is an interlocking end 20. This interlocking end 20 is preferably of a much larger diameter than the feeding tube-engaging end 18. In the embodiment shown in the FIGURES, the interlocking end 20 is cut at an angle of approximately 45 degrees to the axis of the sleeve 14. Interlocking end 20 also includes an interlocking tab 22.

The second component of the present invention is a base elbow unit 24. The base elbow unit 24 is one piece, is preferably molded of plastic, and includes three distinct parts. The first part is a subdermal portion 26, which aids in anchoring the present device when implanted by medical personnel through the ostomy in the patient's body.

The second part of the base elbow unit 24 is a sleeve engaging portion 28 which abuts and is coaxial with, along a first axis, the subdermal portion 26. The outer diameter of the sleeve engaging portion 28 is somewhat larger than that of the subdermal portion 26. Thus, the juncture of the sleeve engaging portion 28 with the subdermal portion 26 forms a flange 30. To ensure a minimum of irritation, this flange 30, which generally abuts the surface of the patient's skin, is smooth and includes beveled or radial edges.

The third part of the base elbow unit is a tube engaging portion 32. As may best be seen in FIG. 4, this tube engaging portion 32 is of a generally elongated and semi-cylindrical, horseshoe shape, with an opening 34 along its length permitting insertion of tube 12. Tube engaging portion 32 is preferably manufactured of a resilient material, such as a nylon or delrin-type polymer. This resiliency enables the opposite, inwardly facing surfaces 36 and 38 (FIG. 4) of the tube engaging portion 32, which surfaces 36 and 38 define the outer edges of opening 34, to move away from one another. This in turn eases the insertion of tube 12 into tube engaging portion 32.

Cylindrical tube engaging portion 32 is disposed along a second axis C which is substantially perpendicular to first axis B. To aid in the immobilization of the tube 12 when the present device is in the fully assembled position and in use by a patient, the first and second axes formed by the tube 12 should define an acute angle, i.e., 90 degrees or less. Thus, it is preferred but not necessary that the first and second axes are perpendicular.

Enteral feeding tube 12 is shown in FIGS. 4 and 4A in what will be termed the assembled or the second, acutely angled position. In contrast, when the subdermal portion 26 of the base elbow unit 24 is initially inserted into the ostomy of the patient, the present device is not in its fully assembled position; rather, the tube is in the first, substantially straight position. As indicated above, when the tube is in this first, substantially straight position, it can move relatively freely through the sleeve 14 and base elbow unit 24. This in turn enables medical personnel to place the outlet end 41 of the enteral feeding tube 12, which may optionally be perforated, at the desired depth within the patient's body.

After proper placement of the outlet end 41 within the patient's body, the tube is moved from the first, substantially straight position of FIG. 3 to the second, acutely angled position of FIGS. 4 and 4A. Both the deformability of the enteral feeding tube 12 and the resiliency of the tube engaging portion 32 enhance the ease with which that tube 12 may be inserted into the tube engaging portion 32. Because the outer diameter of the tube 12 is somewhat larger than the inner diameter of the tube engaging portion 32, and because of the opposing stresses acting upon the tube and tube engaging portion in the position shown in FIG. 4, the tube engaging portion 32 clampingly engages the tube 12 to immobilize it.

As may be seen in FIGS. 4 and 4A, the inner diameter of the cavity 40 defined by the sleeve engaging portion 28 and the subdermal portion 26 of the base elbow unit 24 is at a maximum near the upper end of the sleeve engaging portion 28 and tapers to approximately the diameter of the tube 12 at the lower end of the subdermal portion 26. This feature provides for friction between the tube 12 and the lower end of the subdermal portion 26, thereby inhibiting movement of the tube 12. It also prevents body fluids from entering the tube fixation device near the lower end of the subdermal portion 26. For hygienic purposes, a bactericide or antiseptic is generally placed within this cavity 40 to ensure that bacteria do not grow within it.

After the tube has been placed in its second, acutely angled position and after any bactericide had been placed within cavity 40, sleeve 14 is moved away from the feeding inlet end 16 of tube 12 and towards the base elbow unit 24. The inner diameter of the sleeve must be greater than the outer diameter of the tube engaging portion 32 so that the sleeve can slide over the tube engaging portion 32.

As may be seen in FIGS. 5A, 5B, and 6, the sleeve engaging portion 28 includes an upper tip portion 48 which serves as a mating end for the interlocking tab 22 of the sleeve 14. As the sleeve 14 is pushed towards the sleeve engaging portion 28 of the base elbow unit 24, the angled flats 44 of the sleeve 14 abut and ride upwardly along corresponding flats 46 of the sleeve engaging portion. Because of the angular relationship of these flats, movement of the sleeve towards the sleeve engaging portion results in the rotation of the sleeve from any offset position, as shown in FIG. 5A, to the properly oriented, true position as shown in FIG. 5B. In this true position, the interlocking tab 22 abuts and is aligned with the upper tip 48 of the sleeve engaging portion 28. From this true position of FIG. 5B, a final thrust or push of the sleeve 14 towards the sleeve engaging portion 28 results in the interlocking tab 22 overriding the upper tip 48 so that the tab 22 assumes the detent position depicted in FIG. 6.

In this detent position, the sleeve covers the cavity 40, and thereby affords some protection against the entry of dirt. In this position, the sleeve also affords some protection to any antiseptic or bactericide placed within the cavity 40. Finally, the sleeve 14 in the detent position protects the tube 12 at what may be its most vulnerable point, i.e., at the point where the tube 12 is bent at an acute angle.

As may be seen in FIGS. 3 and 6, interlocking tab 22 includes a lip 50 which engages the upper tip 48. The lip 50 aids in preventing accidental separation of the sleeve 14 from the sleeve engaging portion 28. In fact, in a properly constructed device in accordance with this preferred embodiment, a relatively strong, straight pull on the sleeve 14 while in the detent position should fail to separate it from the sleeve engaging portion 28.

Rather, the sleeve 14 is separable from sleeve engaging portion 28 by imparting a twisting motion. Specifically, the sleeve 14 is grasped and turned in either a clockwise or counterclockwise direction. This results in separation of these two elements because the twisting both moves the lip 50 of the interlocking tab 22 away from and off-center of the tip 48, and also causes angled flats 44 of the sleeve to engage the angled flats 46 of the sleeve engaging portion 28, resulting in an essentially "camming" action. To aid in the secure grasping of the sleeve 14, one or more circumferential ribs 52 may be molded onto or otherwise integrally secured to the sleeve.

While the specific embodiments have been illustrated and described, numerous modifications come to mind without significantly departing from the spirit of the invention and the scope of protection is only limited by the scope of the accompanying claims.

What we claim is:

1. A tube fixation device for the angular fixation of tubes used for the delivery, extraction, or evacuation of fluids or gases through a surgically formed stoma, the tube being generally circular and deformable and having an inlet end and an outlet end, said tube extending outwardly from the patient to carry components of said device, the components of said tube fixation device comprising:
    (a) a sleeve disposed along and movable along said tube towards a base elbow unit, said sleeve having a relatively narrow tube-engaging end frictionally engaging said tube, and said sleeve also having an opposite, interlocking end;
    (b) a base elbow unit through which said tube passes, said base elbow unit including a subdermal portion and a sleeve engaging portion having a common first axis with said subdermal portion, said base elbow unit further including a generally cylindrical tube-engaging portion and oriented along a second axis, said second axis being selectively angled at an acute angle relative to said first axis, the inner diameter of said tube-engaging portion being slightly less than the outer diameter of said tube, and
    wherein said tube is movable from a first, substantially straight position in which said tube passes through and is slidably movable within said subdermal portion and said sleeve engaging portion of said elbow; and a second, selectively angled position in which said tube also passes through said tube engaging portion, and wherein said tube is immobilized by locking engagement to said tube engaging portion, and said tube fixation device further comprising
    (c) an interlocking tab at said interlocking end of said sleeve, said sleeve and said interlocking tab being movable along said tube to a position wherein said tab lockingly engages said sleeve engaging portion of said base elbow unit when said tube is in said second, selectively angled position.

2. The tube fixation device set forth in claim 1, wherein said sleeve includes a plurality of circumferential ribs along the outer surface thereof.

3. A tube fixation device for the angular fixation of a tube used in the delivery, extraction, or evacuation of fluids through a surgically formed stoma in a patient, comprising:
    (a) a generally circular, deformable, elongated tube having an inlet end and an outlet end, said tube extending outwardly from the patient to support additional components of said device;
    (b) a sleeve disposed along and movable along said tube and proximate said inlet end, said sleeve having a relatively narrow tube-engaging end frictionally engaging said tube, and said sleeve also having an opposite, interlocking end;
    (c) a base elbow unit through which said tube passes towards a base elbow unit, said base elbow unit including a subdermal portion and a sleeve engaging portion having a common first axis with said subdermal portion, said base elbow unit further including a generally cylindrical tube-engaging portion and oriented along a second axis, said second axis being at an acute angle to said first axis, the inner diameter of said tube-engaging portion being slightly less than the outer diameter of said tube, and wherein said tube is movable from a first, substantially straight position in which said tube passes through and is slidably movable within said subdermal portion and said sleeve engaging portion of said elbow, and a second, acutely angled position in which said tube also passes through said tube engaging portion, and wherein said tube is immobilized by locking engagement to said tube engaging portion, and further comprising (d) an interlocking tab at said interlocking end of said sleeve, said sleeve and said interlocking tab being movable along said tube to a position wherein said tab lockingly engages said sleeve engaging portion of said base elbow unit when said tube is in said second, acutely angled position.

4. The tube fixation device set forth in claim 3, wherein said sleeve includes a plurality of circumferential ribs along the outer surface thereof.

* * * * *

UNITED STATES PATENT AND TRADEMARK OFFICE
CERTIFICATE OF CORRECTION

PATENT NO. : 4,834,712
DATED : May 30, 1989
INVENTOR(S) : David G. Quinn et al.

It is certified that error appears in the above-identified patent and that said Letters Patent is hereby corrected as shown below:

In Claim 3, Column 6, Line 54, delete "and proximate said inlet end" and insert therefore -- towards a base elbow unit --.

In Claim 3, Column 6, Line 59, delete "towards a base elbow unit" and insert therefore -- and proximate said outlet end --.

Signed and Sealed this

Twenty-fourth Day of July, 1990

Attest:

HARRY F. MANBECK, JR.

*Attesting Officer*  *Commissioner of Patents and Trademarks*